(12) United States Patent
Fennhof et al.

(10) Patent No.: US 6,294,702 B1
(45) Date of Patent: Sep. 25, 2001

(54) METHOD FOR CONTINUOUS PRODUCTION OF DIHYDROXYDIPHENYLALKANES

(75) Inventors: Gerhard Fennhof, Willich; Hans-Josef Buysch, Krefeld; Gerd Fengler, Krefeld; Tony van Osselaer, Krefeld, all of (DE)

(73) Assignee: Bayer Aktiengesellschaft, Leverkusen (DE)

(*) Notice: Subject to any disclaimer, the term of this patent is extended or adjusted under 35 U.S.C. 154(b) by 0 days.

(21) Appl. No.: 09/423,763

(22) PCT Filed: May 5, 1998

(86) PCT No.: PCT/EP98/02644

§ 371 Date: Dec. 13, 1999

§ 102(e) Date: Dec. 13, 1999

(87) PCT Pub. No.: WO98/52896

PCT Pub. Date: Nov. 26, 1998

(30) Foreign Application Priority Data

May 16, 1997 (DE) .............................................. 197 20 541

(51) Int. Cl.⁷ .................................................. C07C 39/12
(52) U.S. Cl. ............................ 568/727; 568/728; 568/749
(58) Field of Search ...................... 536/727, 728, 536/749

(56) References Cited

U.S. PATENT DOCUMENTS

| 2,497,503 | 2/1950 | Jones ..................................... 260/621 |
| 2,775,620 | 12/1956 | Williamson ........................... 260/619 |
| 3,242,219 | 3/1966 | Farnham et al. ...................... 260/619 |
| 4,131,749 | 12/1978 | Kiedik et al. ......................... 568/781 |
| 4,277,628 | 7/1981 | Carnahan .............................. 568/749 |
| 4,308,405 | 12/1981 | Kwantes ............................... 568/727 |
| 4,400,555 | * 8/1983 | Mendiratta ........................... 568/728 |
| 4,594,459 | 6/1986 | Inoue ................................... 568/781 |
| 4,859,803 | 8/1989 | Shaw .................................... 568/727 |
| 4,876,391 | 10/1989 | Kissinger ............................. 568/724 |
| 4,906,789 | 3/1990 | Grzywa et al. ...................... 568/727 |
| 4,935,553 | * 6/1990 | Iimuro ................................. 568/727 |
| 4,954,661 | 9/1990 | Iimuro et al. ........................ 568/727 |
| 5,198,591 | * 3/1993 | Kiedik ................................. 568/727 |
| 5,300,702 | 4/1994 | Perkins et al. ....................... 568/724 |
| 5,315,042 | 5/1994 | Cipullo et al. ....................... 568/727 |
| 5,430,199 | * 7/1995 | Caruso ................................. 568/724 |
| 5,504,251 | * 4/1996 | Dyckman ............................. 568/754 |
| 5,672,774 | * 9/1997 | Dyckman ............................. 568/749 |
| 5,696,295 | 12/1997 | Wulff et al. ......................... 568/724 |
| 5,783,733 | * 7/1998 | Kissinger ............................. 568/724 |
| 6,025,530 | * 2/2000 | Dyckman ............................. 568/754 |

FOREIGN PATENT DOCUMENTS

| 0 017 852 | 10/1983 | (EP) . |
| 0 332 033 | 9/1989 | (EP) . |
| 0 552 518 | 9/1995 | (EP) . |
| 0 630 878 | 3/1998 | (EP) . |

OTHER PUBLICATIONS

Ullmann's Encyclopedia of Industrial Chemistry, 5th edition, vol. A 19, (1993) pp. 348–352, Phenol Derivatives.

Ullmann's Encyclopedia of Industrial Chemistry, 5th edtion, vol. B4. (1993) pp. 321–328, Reaction Columns, Otto Wörz et al.

Ullmann's Encyclopedia of Industrial Chemistry, 5th edition, vol. B3, (1993) pp. 4–70 to 4–92, Distillation and Rectification.

* cited by examiner

*Primary Examiner*—Michael L. Shippen
(74) *Attorney, Agent, or Firm*—Joseph C. Gil; Aron Preis

(57) ABSTRACT

The present invention relates to a process for the continuous production of dihydroxydiphenylalkanes (bisphenols) by the reaction of fresh phenol, and of phenol obtained from the cracking of by-products, with isoalkenylphenol and ketone. In the course of this process, the reaction mixture is worked up by distillation and a high purity bisphenol is produced. The bottom products and distillates containing the by-products are cracked under basic conditions and optionally thereafter under acidic conditions. The cracked products, which substantially consist of isoalkenylphenol and phenol, are recycled, optionally after purification, with the phenol obtained during the purification of bisphenol, to the reaction to form bisphenol, and the residue obtained from cracking is disposed of.

1 Claim, 1 Drawing Sheet

US 6,294,702 B1

METHOD FOR CONTINUOUS PRODUCTION OF DIHYDROXYDIPHENYLALKANES

Figure 1:
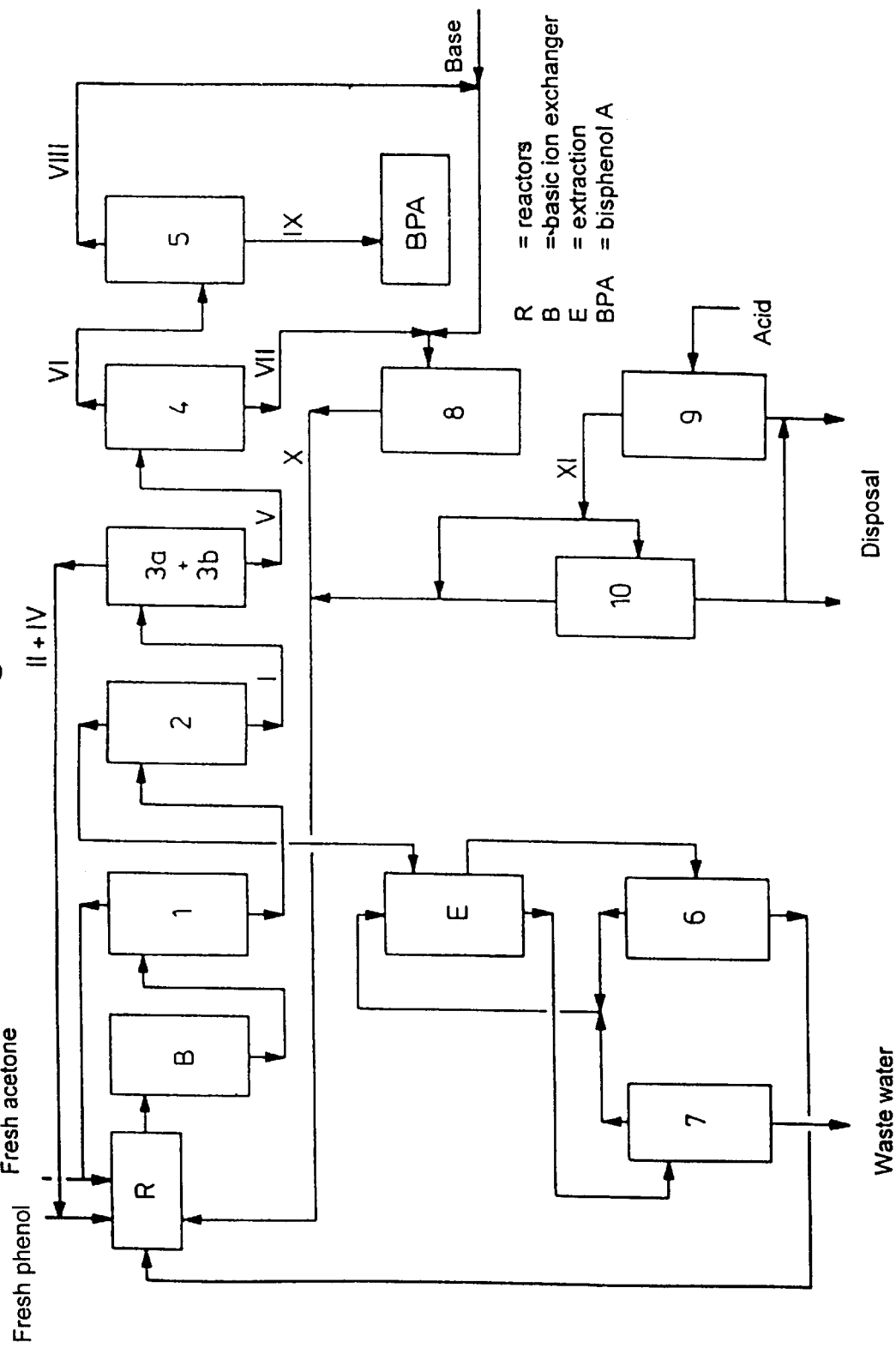

The present invention relates to a process for the continuous production of dihydroxydiphenylalkanes (bisphenols) by the reaction of fresh phenol, and of phenol obtained from the cracking of by-products containing phenol, with isoalkenylphenol and ketone. In the course of this process the reaction mixture is worked up by distillation and a high-purity bisphenol is produced. The bottom products and distillates containing the by-products are cracked under basic conditions and optionally thereafter under acidic conditions. The cracked products, which substantially consist of isoalkenylphenol and phenol, are recycled, optionally after purification, with the phenol obtained during the purification of bisphenol, to the reaction to form bisphenol. The residue obtained from cracking is disposed of.

It is known that bisphenols can be produced by the acid-catalysed reaction of ketones with phenol. There is a series of different proposals which have been made for this purpose (see U.S. Pat. No. 2,775,620, EP-A 342 758, EP-A 616 993, DE-OS 38 33 900, U.S. Pat. No. 4,308,404, U.S. Pat. No. 4,308,405, EP-A 630 878, U.S. Pat. No. 4,876,391, U.S. Pat. No. 3,242,219, for example).

In Ullmann's Encyclopedia of Industrial Chemistry, 5th Ed., Vol. A19, pp. 348–52, there is a review of the prior literature on the production of bisphenol. As a rule, bisphenols, particularly bisphenol A. which is the most important commercially of the bisphenols, are produced by adding ketone and phenol to a circulating mother liquor from the work-up of bisphenol passing this mixture over acidic ion exchangers and carrying out the reaction to produce bisphenol. Unreacted ketone is optionally recovered from the reaction mixture and is recycled to the reaction. The reaction mixture is cooled, and the bisphenol is crystallised out, optionally as a phenol addition compound, and is separated and washed with phenol. The phenol is separated from the addition compound by flash distillation and pure phenol is obtained. The mother liquor from the crystallisation stage is passed over acidic ion exchangers and any isomers which it contains are rearranged to form bisphenol. The bisphenol which is produced in this manner is separated by crystallisation, and the crystallised product obtained is transferred to the first crystallisation stage. Part (about 10 to 20%) of the mother liquor which is then obtained is separated and the bulk is recycled to the reaction. Phenol is distilled from the part which is separated and is recycled to the reaction. The residue obtained on distillation is removed from the process and is used for the production of phenolic resin, for example.

In this procedure, which is relatively complicated, the mother liquor is recycled time after time over the catalyst. This gives rise to many isomers and by-products, and also results in coloured compounds. The latter have to be carefully separated from bisphenol. which possibly makes a further crystallisation stage necessary. In addition, appreciable amounts of valuable compounds such as bisphenol and isomers are lost with the part which is separated and which is finally removed from the process. This removal from the mother liquor is absolutely necessary in order not to allow the amount of unusable contaminating compounds to become too large.

Attempts have therefore been made to subject the fraction which is removed from the process to work-up and cracking in order to recover valuable substances for the production of bisphenol. There has also been a series of proposals for this purpose. According to U.S. Pat. No. 2,497,503, phenols and alkenylphenols which still have to be carefully purified can be obtained in moderate yield by pyrolysis at about 300° C. According to the teaching of EP-A 17 852, a hydrogenation treatment also results in valuable products. The cracking process can also be speeded up by acidic and basic compounds. However, with acids such as sulphuric or toluenesulphonic acid, only phenol is obtained (U.S. Pat. No. 3,466,337). In contrast, basic catalysts result in the cracking of materials removed from the process into phenol and isoalkenylphenol. The following have been cited as catalysts: alkali compounds such as NaOH, KOH, $NaHCO_3$, Na acetate, Na hypophosphite. $K_2CO_3$, MgO and Al isopropylate (U.S. Pat. No. 4,277,628, U.S. Pat. No. 4,594,459, U.S. Pat. No. 4,131,749). When this procedure is used, however, only part of the material removed from the process is cracked, and a batch or semi-continuous process is employed. Completely continuous processes are unknown.

These processes have been improved as regards a higher purity of the bisphenol by feeding the phenol/isoalkenylphenol mixture from the cracking stage into the first mother liquor after separating the first bisphenol fraction. The mixture is passed over the acidic catalyst, and both rearrangement and the reaction of isoalkenylphenol with phenol are allowed to proceed simultaneously. The second bisphenol fraction is then separated from the mixture by crystallisation, and the second mother liquor is recycled to the cracking stage. Tile second bisphenol fraction is fed to the first crystallisation stage. The purity of the bisphenol is thereby increased somewhat, but the process is complicated by a further recycling stage (U.S. Pat. No. 4,954,661).

It has also been proposed that the second mother liquor in the aforementioned bisphenol process, or the first mother liquor after separating the first amount of bisphenol and alter rearrangement be worked-up at least in part by distillation in order to achieve better utilisation of the valuable products contained therein. The bisphenol which is thus obtained is recycled to the first crystallisation stage and is purified there. The low-boiling fractions which contain isomers are fed to the reaction (WO 94/20 445 and EP-A 552 518). The difficulty consists of obtaining fractions which are sufficiently pure, and which arc particularly low in difficultly separable chromanes and indanies, from the mother liquor, which is considerably enriched in isomers and by-products, at a justifiable cost, without overly increasing the amount of residue which can no longer be used and without reducing the yield. A part of the distillation products therefore has to be rejected. The fractions low in bisphenol which are obtained on distillation can also be subjected to cracking, and the cracked products can be recycled to the process (EP-A 332 033).

It has also been proposed that bisphenol which originates from the first crystallisation stage in the aforementioned bisphenol process be purified further by distillation, whereby a high-purity (up to 99.985%) bisphenol is obtained (EP-A 679 626).

It has now been found that an outstanding yield of bisphenol of high purity is obtained, by a simple, completely continuous process, if phenol is reacted with ketone and isoalkenylphenol from the cracking stage so that as few as possible isomers and by-products are formed, this reaction product is freed from acidic constituents if necessary water of reaction and residual acetone are distilled off, the reaction mixture is concentrated by evaporation and phenol is recovered for the reaction process, the residue obtained is separated in an efficient distillation column into a distillate containing low-boiling fractions and bisphenol and into a bottom product containing high-boiling fractions, the distillate is separated in a further column into a low-boiling distillate and into a bottom product which constitutes high-purity bisphenol, the low-boiling distillate is combined with the high-boiling fractions from the first column, is treated with a basic catalyst and is continuously cracked in a reactive rectification stage. The distillate containing phenol and isoalkenylphenol is fed to the bisphenol reaction. The bottom product is acidified if necessary and is subjected to a second cracking procedure in a further reactive rectification stage, whereupon phenol passes over and an unusable residual bottom product is formed.

The starting materials for the process according to the invention are aromatic hydroxy compounds and ketones.

Aromatic hydroxy compounds which are suitable for the process according to the invention are not substituted in the p-position and contain no second order substituents such as cyano, carboxy or nitro groups; suitable examples include phenol, o- and m-cresol, 2,6-diimethylphenol, o-tert.-butylphenol, 2-methyl-6-tert.-butylphenol, o-cyclohexylpihenol, o-phenylphenol, o-isopropylphenol, 2-methyl-6-cyclopentyl-phenol, o- and m-chorophenol. and 2,3,6-trimethylphenol. Phenol, o- and m-cresol, 2,6-dimethylphenol, o-tert.-butylphenol and o-phenyl-phenol are preferred; phenol is particularly preferred.

Suitable ketones contain at least one aliphatic group on their carbonyl function; examples include acetone, methyl ethyl ketone. methyl propyl ketone, methyl isopropyl ketone, diethyl ketone, acetophenone, cyclohexanonle, cyclopentanone, and methyl-, dimethyl- and trimethylcyclohiexanones, which may also contain geminal methyl groups, such as 3,3-dimethyl-5-methylcyclohexanone (hydro-isophorone).

Acetone, acetophenone, cyclohexanone and homologues thereof which contain methyl groups are preferred; acetone is particularly preferred.

Catalysts which are suitable for basic cracking are cited in the literature, and are preferably alkali oxides and hydroxides, most preferably NaOH and KOH. In the process according to the invention, these are introduced into the melt of the cracking products and are dissolved and homogeneously distributed, wherein the temperature is advantageously between 100 and 200° C. preferably between 120 and 180° C.

Catalysts which are suitable for acidic cracking are listed in the literature, and preferably comprise sulphuric acid, phosphoric acid and phosphorous acids, partial salts thereof such as $NH_4HSO_4$, $NaHSO_4$, $KHSO_4$, $NaH_2PO_4$, $KH_2PO_4$, $NH_4H_2PO_4$, $NH_4H_2PO_3$, $KH_2PO_3$ and analogues thereof, and also organic derivatives of these acids, namely aromatic sulphonic acids and disulphonic acids such as benzene-, toluene-, xylene- and phenolsulphonic acids, diphenyldisulphonic acid and diphenyl ether-disulphonic acid, as well as aromatic phosphonic and phosphinic acids such as benzene-, toluene- and xylene-phosplhonic and -phosphinic acids, diphenyl-diphosphonic and -diphosphinic acids, and also solid acids such as acidic aluminas, argillaceous earths such as bentonite and montmorillonitephenol, zeolites, titanium and zirconium oxides, and niobium and tantalum oxides; acidic aluminas are preferred.

The amounts of catalysts which are supplied to the mixture to be cracked are between 0.01% by weight and 5% by weight, preferably between 0.05% by weight and 3% by weight, most preferably between 0.1% by weight and 2% by weight, with respect to the amount of mixture to be cracked. So as to be able to adhere to this quantitative rule for acidic catalysts, the basic catalysts either have to be removed from the bottom product after basic cracking, which would generally be too costly, or they first have to be neutralised by a strong acid. In this manner, it is ensured that sufficient amounts of active acid are present. Acidification in the sense of the present invention therefore means that an amount of acid is added to the bottom product such that the basic catalyst contained therein is neutralised and moreover a sufficient amount of acidic catalyst is available for the following acidic cracking stage.

The catalysts can be continuously added, dissolved or suspended in phenol, to the stream flowing in the crackin column. for example. However, it is also possible, to admix them batch-vise, in intermediate vessels, with the material to be cracked, and then to feed this mixture continuously into the column.

The columns in which the reactive rectification is carried out correspond in general to customary distillation columns. In these columns, cracking is accompanied by the separation of the cracked products, namely phenol and isoalkenylphenol, from the uncracked or uncrackable compounds by distillation and fractionation. In the course of this procedure the cracked products pass overhead, and are generally already pure enough for further use. The uncrackable fractions are discharged as a bottom product. Reactive rectification operations are known to one skilled in the art and are described in Ulimann's Encyclopedia of Industrial Chemistry, 5th Ed., Vol. B4, pp. 321–8, for example.

In the present case it may be advantageous proportionally to reduce the column diameter in the bottom part, corresponding to the volume of liquid and Gas which decreases from top to bottom in the columns during cracking. In order to achieve a suitable dwell time of the cracked material in the column, it is advisable to include plates in the cracking columns. This applies in particular to the part in which cracking proceeds. The use of packed bodies or packing materials in the top part may be indicated in order to achieve effective separation of the products.

In the event that the phenol which distils from the second column is still not sufficiently pure for use in the synthesis of bisphenol, it can be introduced into a further column or into the first cracking column and purified still further there.

The preferred procedures for the reaction to formn bisphenol are those which provide bisphenol in a manner wvhich is as highly selective as possible. They are characterised in that the lowest possible temperature and the lowest possible ketone concentration are employed.

This can be achieved by reacting phenol with ketone and isoalkenylphenol in at least two reactors which are connected in series and which contain acidic ion exchangers, and which are operated at the lowest possible temperature but in the sense of progressive reaction with increasing temperature, wherein the total amount of ketone and isoalkenylphenol is apportioned into the separate reactors and is homogeneously distributed in the reaction mixture before entering the respective reactors. The selectivity for bisphenol can be increased even further if the distribution of ketone and isoalkenylphenol is controlled so that tile proportion of the total amount per reactor is less the higher is the temperature of the reactor in question, and if the reactor cascade is operated within a maximum temperature range of 35 to 85° C., preferably 38 to 75° C.

The separate reactors are advantageously preceded both by mixing units of known type of construction, to ensure the homogeneous distribution of ketone and isoalkenylphenol in the initial phenol or reaction mixture, and by heat exchangers to bring the mixture to the desired temperature before it passes through the catalyst bed.

The process according to the invention is explained with reference to FIG. 1. After leaving the last reactor in the cascade, or after the separation of ketone, the reaction mixture should be freed from acidic constituents as described in EP-A 552 518 or in U.S. Pat. No. 4,876,391, for example. If necessary, a fine filtration step should also be carried out in order to remove catalyst and apparatus detritus and other solid contaminants. The water of reaction and unreacted ketone is then distilled from the reaction mixture, with the ketone being recycled to the reaction. The water, which contains phenol, is freed from phenol by extraction and is disposed of. The phenol-containing extract is separated by distillation, phenol is fed to the reaction and the extractant is recycled to the extraction apparatus. These procedures are known to one skilled in the art.

The reaction mixture which then results is very substantially freed, in two stages under reduced pressure. firstly from the bulk of the phenol and then from residual phenol, wherein the bottom temperatures of the columns should not exceed about 250° C. and the pressures should be <400 mbar, particularly <300 mbar. The phenol which is distilled off in this manner is fed to the reaction. The bottom product, which contains compounds with boiling points higher than that of phenol, is fed approximately to the middle of a column which represents 25 to 50 plates depending on the manner of operation, and is then separated into a distillate containing the low-boiling fractions such as isomers, chromanes and bisphenol, and into a bottom product containing the high-boiling fractions such as indanes, spiro-bis-indanes, trisphenol and residual bisphenol. The distillate is separated, in a further column which is similar to the first and which comprises 25 to 50 plates, into a low-boiling distillate and into a bottom product containing high-purity (>99.8%) bisphenol. The last-mentioned distillate, which contains the isomers. and the bottom product from the separation of bisphenol by distillation. which contains the high-boiling fractions and residual bisphenol, are combined, and after the addition of basic catalysts they are fed completely continuously to a reactive rectification stage and are cracked there at bottom temperatures of 190 to 270° C., preferably 200 to 260° C., most preferably 210 to 250° C., and at pressures of 15 to 0.5 mbar. preferably 12 to 1 mbar. most preferably 10 to 1 mbar. The distillate, which consists of phenol and isoalkenylpheriol and oligomers thereof, is fed to the reaction. The bottom product is fed. after acidification, to a second reactive rectification stage similar to that mentioned above, and is cracked there at 150 to 260° C., preferably 160 to 250° C., most preferably 170 to 240° C., and at the pressures given above, whereupon phenol is distilled off and can optionally be further purified via a column and admixed with the reaction stream, and a bottom product which is to be disposed of is taken off at the base of the column.

If the proportion of bottom product from basic cracking is too low for the economical operation of a column, on account of a production stream of a bisphenol plant being relatively small, it is recommended that small amounts such as these from a plurality of streams are combined, or that the bottom product from a plant is accumulated to form a larger amount, followed by the cracking thereof in a suitable apparatus.

If the water of reaction which is unavoidably formed is excluded from the mass balance from the outset, yields of material of up to 99% can be obtained by the process according to the invention as described above; moreover, a particularly pure bisphenol is obtained.

The distillation apparatuses used correspond to the prior art and are known to one skilled in the art. Packed bodies, preferably the packing materials which are described in Ullmann's Encyclopedia of Indust. Chem., 5th Ed. Vol B3, pp. 4–70 to 4–92, are used in the columns for the separation of bisphenol. The cracking columns may also contain packed bodies and packing materials, particularly in the top part in which fractionation is effected. Plates are preferred in the bottom part, however, and these are also described in Ullmann's Encyclopedia (loc. sit.).

The reaction mixtures leaving the reactor cascade, which are to be used in the distillation, may contain 10 to 35% by weight, preferably 12 to 32% by weight, most preferably 14 to 30% by weight, of bisphenol. The content of bisphenol in the reaction mixture which is freed from phenol should be not less than 90% by weight.

Compared with known bisphenol processes, the process according to the invention accordingly has the advantages of providing a high-purity bisphenol in an extraordinarily high yield, whilst being conducted in a considerably more simple manner and completely continuously.

EXAMPLE (SEE FIG. 1)

BPA was produced in a cascade of three reactors (R), which were packed with acidic ion exchangers (SC 102, Bayer AG) containing 3.6% by weight dimethylthiazolidine as a co-catalyst. by introducing about 18,665 parts by weight/hour of phenol, well mixed with 600 parts by weight/hour of acetone and with 283 parts by weight/hour of distillate from the residue cracking stage containing about 140 parts by weight isopropenylphenol and oligomers thereof, into the first reactor, which was at a temperature of 55° C., with an amount of catalyst corresponding to 0.6 kg/liter.hour of product. The product leaving the first reactor was well mixed with 400 parts by weight/hour of acetone and with 187 parts by weight/hour of distillate from the residue cracking stage containing about 93 parts by weight/hour of isopropenylphenol (oligomers). was brought to a temperature of 65° C., and was fed into the second reactor. likewise with 0.6 parts by weight/l.hour. The product flowing from the second reactor was well mixed with 200 parts by weight/hour acetone and with 94 parts by weight/hour of distillate from the residue cracking stage containing about 46 parts by weight of isopropenylphenol (oligomers), was brought to a temperature of 75° C., and was fed into the third reactor, likewise with 0.6 parts by weight/liter.hour.

The acetone conversion was then 97 to 98% theoretical. The reaction mixture was passed over a bed of basic ion exchanger in order to remove traces of acidic compounds, and was then freed from water and residual acetone.

The reaction mixture (20,297 parts by weight/hour) from this reaction of phenol with acetone and isopropenylphenol, which had the composition 1 given in Table 1 and which had already been freed, in a first distillation unit (1+2), from water of reaction containing a little phenol and residual acetone (phenol was recovered from the distillate by extraction (E) and subsequent work-up by distillation (6,7) and was recycled to the reaction), was continuously separated from the bulk of the phenol (12,746 parts by weighlt/hour, II) in the first column (3a) of a second distillation unit (3) consisting of two columns connected in series, and the bottom product obtained (7,821 parts by weight/hour, III) was very substantially separated from phenol (3,308 parts by weight/hour, IV) by a third distillation in a third column (3b).

The two phenol distillates II and IV were recycled to the BPA reaction. The bottom product (4513 parts by weight/hour, V) was fed approximately into the middle of a column (4) comprising 30 to 40 separating stages and was separated, at a top temperature of about 215° C. and at a bottom temperature of about 247° C. and at 5 mbar, into a distillate rich in BPA (4134 parts by weight/hour, VI) and into a bottom product which contained the highi-boiling fractions (302 parts by weight/hour, VII). The distillate was fed approximately into the middle of a column (5) which likewise comprised 30 to 40 separating stages, and the fraction with a boiling point lower than that of BPA (300 parts by weight/hour, VIII) was distilled off at 5 mbar and at a top temperature of about 204° C. and a bottom temperature of about 242° C., whereupon BPA of high purity (3824 parts by weight/hour, IX) was then obtained in the bottom product. Bottom product VII and distillate VIII (602 parts by weight/hour) were continuously treated with 0.2% by weight KOH, injected approximately into the middle of a 20-plate column (8) and were cracked at 8 mbar, at a top temperature of 82 to 85° C. and at a bottom temperature of 230 to 235° C. The distillate (525 parts by weight/hour, X) was fed to the reaction with phenol to form BPA. After the addition of 2 moles toluenesulphonic acid per mole of KOH present, the bottom product (76 parts by weight/hour) could be further cracked in a final column (9), which likewise contained 20 plates, by injecting it approximately into the middle of the column, at 4 to 5 mbar and at a top temperature of about 71 to 4° C. and a bottom temperature of about 200° C., whereupon a phenol distillate (39 parts by weight/hour, XI) was produced which was likewise fed to the BPA reaction (optionally after purification in column 10), and a residue (37 parts by weight/hour) was formed which was disposed of.

Therefore, during the production of 3824 parts by weight/hour BPA, 37 parts by weight/hour of by-product were produced, corresponding to a yield of material of >98%.

What is claimed is:

1. A continuous process for the production of dihydroxydiarylalkane comprising (i) reacting an aromatic hydroxy compound with at least some ketone and at least some isoalkenylphenol at the lowest possible temperature in a first of a cascade of at least two reactors to form a reaction mixture and continuing the reaction at increasing temperature in the succeeding at least one reactor into which ketone and isoalkenylphenol are apportioned, and removing acidic constituents from the reaction mixture, and (ii) distilling water of reaction and residual ketone from the reaction mixture to form a dry reaction mixture, and (iii) distilling phenol from said dry reaction mixture to obtain a first bottom product, and (iv) distilling said first bottom product to obtain a distillate rich in dihydroxydiarylalkane and a second bottom product containing high-boiling fractions, and (v) distilling said distillate to obtain a second distillate containing fractions which are lower-boiling than dihydroxydiarylalkane and to obtain a third bottom product containing bisphenol, (vi) combining said second bottom product with said second distillate to form a combination and continuously cracking said combination in the presence of a base, in a multi-step reactive distillation, to produce (a) phenol and isoalkenylphenol which pass overhead and (b) a high-boiling bottom product, (vii) acidifying and cracking said high-boiling bottom product in reactive distillation, to produce phenol and resin, and

TABLE 1

|  | o,o'-BPA | o,p'-BPA | Chromane | p,p'-BPA | Indane | Tris-phenol | MG402 | NP | ΣIPENP | Phenol | Parts by wt./hour |
|---|---|---|---|---|---|---|---|---|---|---|---|
| I | 0.02 | 0.85 | 0.06 | 21.89 | 0.07 | 0.19 | 0.11 | 0.10 |  | 76.71 | 20297 |
| II | 0 | 0.01 | 0 | 0.03 | 0 | 0 | 0 | 0 |  | 99.96 | 12476 |
| III | 0.05 | 2.34 | 0.14 | 56.09 | 0.19 | 0.55 | 0.29 | 0.36 |  | 39.98 | 7821 |
| V | 0.07 | 3.14 | 0.21 | 93.03 | 0.33 | 0.95 | 0.51 | 0.60 |  | 1.18 | 4513 |
| VII | 0 | 0 | 0 | 67.68 | 4.41 | 13.08 | 7.02 | 7.91 |  | 0 | 302 |
| VIII | 1.12 | 44.33 | 2.77 | 51.71 | 0 | 0 | 0 | 0 |  | 0.07 | 300 |
| IX | 0 | 0.005 | 0.015 | 99.97 | 0.008 | 0 | 0 | 0 |  | 0 | 3824 |
| X | 0.02 | 0.06 | 0.07 | 0.28 | 0.02 | 0 | 0 | 0 | 53.16 | 46.31 | 525 |
| XI | 0 | 0.02 | 0.18 | 0.09 | 0.11 | 0 | 0 | 0.18 | 0 | 99.60 | 39 |

(viii) recycling the phenol distillate obtained in (vii) and the phenol and isoalkenylphenol produced in (vi), optionally after purification, to said reaction mixture said aromatic hydroxy compounds being unsubstituted in the p-position and containing no second order substituents.

* * * * *